United States Patent [19]

Colburn, Jr.

[11] Patent Number: 5,033,397

[45] Date of Patent: Jul. 23, 1991

[54] SOIL CHEMICAL SENSOR AND PRECISION AGRICULTURAL CHEMICAL DELIVERY SYSTEM AND METHOD

[75] Inventor: John W. Colburn, Jr., Houston, Tex.

[73] Assignee: Aguila Corporation, Houston, Tex.

[21] Appl. No.: 562,210

[22] Filed: Jul. 31, 1990

[51] Int. Cl.[5] ............................................. A01C 23/00
[52] U.S. Cl. ...................................... 111/118; 47/1.3; 204/400; 324/347
[58] Field of Search .............. 47/1, 1.3, 118, DIG. 10, 47/1.01; 73/151, 153, 864.58; 175/50; 204/400, 403; 324/347, 376; 364/420, 421, 422; 111/1, 6, 7, 118

[56] References Cited

U.S. PATENT DOCUMENTS

| | | | |
|---|---|---|---|
| 2,454,952 | 11/1948 | Starkey et al. | 47/1.3 X |
| 3,625,166 | 12/1971 | Woodley | 111/7 |
| 3,723,989 | 3/1973 | Fathauer et al. | 111/1 |
| 3,877,401 | 4/1975 | Gutman | 111/7 |
| 4,015,366 | 3/1977 | Hall, III | 364/172 X |
| 4,333,096 | 6/1982 | Jenkins | 111/1 |

Primary Examiner—Brian S. Steinberger
Attorney, Agent, or Firm—D. Arlon Groves

[57] ABSTRACT

A real time soil chemical sensor and precision agricultural chemical delivery system includes a plurality of ground-engaging tools in association with individual soil sensors which measure soil chemical levels. The system includes the addition of a solvent which rapidly saturates the soil/tool interface to form a conductive solution of chemicals leached from the soil. A multivalent electrode, positioned within a multivalent frame of the ground-engaging tool, applies a voltage or impresses a current between the electrode and the tool frame. A real-time soil chemical sensor and controller senses the electrochemical reaction resulting from the application of the voltage or current to the leachate, measures it by resistivity methods, and compares it against pre-set resistivity levels for substances leached by the solvent. Still greater precision is obtained by calibrating for the secondary current impressed through solvent-less soil. The appropriate concentration is then found and the servo-controlled delivery system applies the appropriate amount of fertilizer or agricultural chemicals substantially in the location from which the soil measurement was taken.

25 Claims, 2 Drawing Sheets

SOIL CHEMICAL SENSOR AND PRECISION AGRICULTURAL CHEMICAL DELIVERY SYSTEM AND METHOD

This invention was made with Government support under Contract No. DE-AC07-84ID12518 awarded by the Department of Energy. The Government has certain rights in this invention.

RELATED PATENT APPLICATIONS

This application is related to co-pending U.S. patent application Ser. No. 07/275,266 filed Nov. 23, 1988, now abandoned, which in turn was related to then-copending U.S. patent application Ser. No. 07/076,055 filed July 21, 1987, which was abandoned upon filing of related application 275,266.

BACKGROUND OF THE INVENTION

The present invention relates to a novel agricultural chemical system and method and, more particularly, to a system that senses the chemical condition of the soil in real time and applies an appropriate amount of corrective agricultural chemical or fertilizer in response to a sensed deficit or excess condition. This system has important benefits in cost reduction, energy resource conservation, crop production, and reduction of environmental degradation.

The modern farm practice of applying chemicals to the soil to obtain optimal crop yield differs little from that used a hundred years ago, when manure from farm animals and so-called "green manure" (composed of luguminous crops or harvest detritus) were added. The farmer, as always, desires sufficient soil fertility to ensure that a successful harvest will result from his planting. The methods by which the farmer's objectives are met have advanced considerably. Cropland productivity is increased many-fold with the application of specific chemical materials tailored to precisely provide the plant nourishment or protection needed. Beyond the need for adequate fertility, the crop is usually also given protection from competing weeds and insects by the application of assorted herbicides and insecticides.

Fertilizers and agricultural chemicals are applied by diverse types of field equipment, including granular spreaders, liquid spray bars, and anhydrous, solution, or granular injectors. Farmers also make choices as to when to apply the fertilizer for the next growing season, such as in the late fall or early spring, while planting, or after planting. Similarly, agricultural chemicals such as herbicides are applied at an appropriate stage of weed growth most likely to destroy or regulate undesireable plant growth.

Assorted variables influence the amount of nitrogen and other nutrients that are available for plant growth and development. In the case of nitrogen, local field conditions determine the quantity of ammonium held on the exchange complex of the soil and the precise mechanics of conversion to more available forms via bacterial action. Conversion of variable ammonium levels at distributed oxidation levels in soils is highly variable from point-to-point even within fields which appear relatively homogeneous. Although this extreme variability of soil chemical levels has been known since at least the 1920's, until now no one has perfected a method of accounting for this variability while adding fertilizers or other corrective chemicals such as lime.

Nitrogen exists in the soil in a variety of chemical forms. In the ammonium form it is relatively immobile, but after transformation by soil bacteria to nitrate its mobility increases drastically. Nitrate becomes elusive because of its high solubility in soil water. Nitrate moves with the soil water in response to soil temperature changes, rainfall, and crop transpiration demands. The coefficient of variation of soil nitrate levels typically has a mean of 50% and often reaches 100% even over small areas of only several square yards. Similar observations have been made for pH and potassium levels. Because available nitrogen varies widely, even when fields have been uniformly fertilized, sporadic, conventional soil samples cannot be representatve indicators of a field's nitrogen availability status.

Insufficient nutrient levels will affect crop productivity adversely; excess nutrient levels will either have a similar effect or simply be wasted. In the case of nitrogen, soil nitrate ($NO_3$—N) levels above 30 ppm are considered to be wasted nutrients. Field data indicate that considerable excess nitrate is available that does not contribute to crop production. Because nitrate is mobile and does move downward away from the rooting zone in the absence of a crop, nitrate in the soil at the end of a growing season may not be available to the next year's crop but may serve only to contaminate ground water.

Plants use only those nutrients they need and the use of the nutrients complies with a law of diminishing returns. Above a certain threshold level, the farmer obtains little yield response with increasing nutrient level. From an energy efficiency perspective, nutrients applied above this threshold level are wasted. In the case of a normal distribution with a large coefficient of variation (ratio of standard deviation to the mean value), approximately 50% of the nutrients are wasted. This means that both the energy and raw materials used to manufacture the nutrient, as well as the farmer's profit dollars, have been squandered.

For example, nitrogen in its gaseous form is of no use to plants. Plants require that nitrogen, in the form of complex nitrogen compounds, be further transformed into soluble nitrates in order to be utilized by the plants. All agricultural chemical compounds, including manure, are toxic to some extent and can contaminate groundwater, particularly those in the nitrate form. Thus amounts of fertilizer greatly in excess of what the plants can profitably use cannot be prudently applied. They are also expensive, which is another good reason to not overfertilize cropland. Until the present invention, the farmer has had no practical way to optimize his application rate, nor to vary his application rate in response to changing conditions across his field. He has been limited to simply applying what worked in the past, perhaps aided by his recollection of how last year's crop came out, perhaps supplemented by a few spot soil analyses made around the field.

Because of the spatial variations in his field, and because of the time delay between sampling and receiving results—during which the soil conditions will have changed—the farmer who has paid for spot samples is scarcely better able to fertilize his fields than is the farmer who simply fertilizes on an historic basis. Consequently, farmers routinely apply excess fertilizer as a protective measure, and in doing so lower their profit margin and risk groundwater contamination, neither of which is desirable.

Farmers know, qualitatively, that crop yields vary because uniformly applied fertilizers are not converted uniformly to forms useful to plants. Farmers generally use rules of thumb to guide application timing. Moreover, farmers realize that their only source of agrichemical recommendations beyond accepted rules of thumb is either an extension agent or a chemical sales representative.

Soil sampling, used to aid the farmer in fertilizer application, is conventionally based on a farmer's own sample timing and site selection rationale. Chemical analyses of soil samples that the farmer provides to the extension system agent or salesman require interpretation by technically trained personnel to reveal nutrient needs. Often, however, either no nutrient analysis is performed or the analysis is ignored as meaningless due to the perceived complexity of the technical issues in agricultural chemical management. Today, generalized nitrogen management recommendations are all based on experimental evaluation of different fertilizer treatment methods. Soil tests are not routinely done for available nitrogen at the farm level, and the "turn-around" time between sampling and receiving laboratory results is too long to satisfy the farmer's needs for the timing of his application. Local, spatial variations which have significant effects on the crop are normally not addressed at all.

Accordingly, significant energy waste occurs in the application of agricultural chemicals simply because no proven, economical method exists to properly and timely allocate chemicals to meet crop needs, and agricultural chemicals and fertilizers are consequently applied in substantially uniform amounts irrespective of local variations in soil chemical conditions.

In summary, the conventional method of providing agrichemical recommendations for farm level chemical application includes soil sampling by the farmer himself and laboratory analyses, resulting in technically informed interpretations by technically trained personnel. These recommendations normally are then implemented by the farmer himself, who usually is not technically trained in these disciplines.

There are significant sources of error in this multiple-step process, including, for example, errors unavoidably caused by the time delay and errors in selecting a truly representative sample, sample collection and handling, sample preparation and conditioning in the laboratory, trained interpretation of nutrient needs, and errors in application of the recommended level due to the imprecision of the chemical application equipment.

OBJECTS OF THE INVENTION

It is therefore a principal object of the present invention to provide a rapid soil chemical sensor and application control system to apply fertilizer and other agricultural chemicals to timely meet crop and farmer profitability and environmental needs on a local basis within a field while a farm chemical application vehicle traverses the field.

It is another object of the present invention to provide a soil chemical sensor and application control system that utilizes a low cost, fast response detector that can be applied to or integrated with a variety of ground engaging tools to detect soil nutrient levels.

Still another object of the present invention is to provide a soil chemical sensor recommendation system and a precision application control system that operates while a farm vehicle traverses a field without substantial intervention by the vehicle operator.

SUMMARY OF THE INVENTION

In one embodiment, the soil chemical sensor system of the present invention may be used by itself to accurately determine soil deficit or excess conditions on a spot basis or throughout a field for later correction. Preferably, however, it will be used with one or more ground-engaging tools in association with individual soil chemical sensors. In a preferred embodiment, a solvent is applied while the tool or tools are moving past a soil sample, which rapidly saturates the soil/tool interface to form a conductive slurry containing dissolved chemicals (leachate) extracted from the soil. Preferably, a multi-valent electrode, positioned within a multivalent frame (such as iron) of the ground-engaging tool, applies a voltage differential or impresses a current between the electrode and tool frame; a real-time soil chemical sensor controller reacts to the electrochemical current resulting from the application of the voltage differential or current across the leachate and the local soil sample. This transfer, which may be measured by resistivity methods, is preferably compared to calibrated resistivity magnitudes for target substances extracted by the solvent and applied voltage differential or current. If the user has specified a maximum allowable concentration, the appropriate proportion of this maximum is then found and the servo-controlled applicator applies the appropriate amount of fertilizer or agricultural chemicals in close proximity to the location from which the soil measurement was taken. If a nutrient level in excess of the maximum allowable value is sensed, nothing is applied.

DETAILED DESCRIPTION

It is to be understood that the soil chemical sensor and agricultural delivery system of the present invention, when used to apply fertilizer, for example, may automatically, without tractor operator interaction, apply the needed chemicals to soil regions with low soil chemical levels to bring said levels to the desired level. The system may be most advantageously used by applying the bulk of fertilizer a few weeks after crops emerge, as opposed to the conventional approach which applies high, uniformly applied pre-plant fertilizer levels. Post-plant application is demonstrated to be much more efficient than pre-plant application, but has hitherto been difficult to control properly. In the case of nitrogen fertilizer, ammonium after conversion to nitrate becomes the representative parameter for crop nitrogen fertility. It would be preferable to measure and dispense in response to nitrate, in contrast to other nitrogen species such as ammonium which may also be determined by the method disclosed herein. Furthermore, this system permits the introduction of nitrogen nearer the time in the growing cycle that the crop needs the nutrient. As a result, fertilizer is more efficiently used and less fertilizer may be used to achieve a given increase in productivity.

Figure 1:
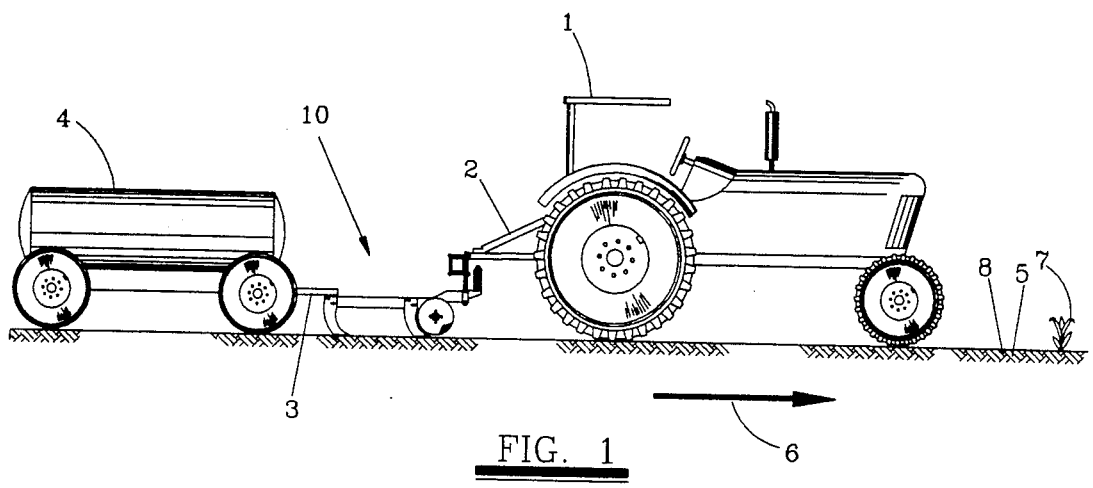
FIG. 1 is a simplified pictorial representation of a preferred embodiment of the soil constituent sensor and chemical application system of the present invention in a typical field operation.

Referring now to FIG. 1, there may be seen a simplified pictorial representation of one type of system embodying the concepts of the present invention for sensing soil constituent levels and dispensing the needed amount of corrective chemical. More particularly, there may be seen a farm chemicals application vehicle 1, commonly a farm tractor, flexibly and removably attached by adjustable lifting means 2, commonly a three-point hitch, to sensing and dispensing system 10. The resulting assemblage is shown being operated in direction 6 over farm soil 5 in which crops 7 are grown and measuring the concentration of desired soil chemical 8 and supplying farm chemicals withdrawn from a reservoir 4 removably attached to the frame of the application vehicle attached by hitch means 3. Crops 7 may include row crops, grasses, orchard crops, vineyards or any other type of crop in which a mobile vehicle can routinely traverse the field and for which a soil chemical level and chemical application are appropriate.

Figure 2:
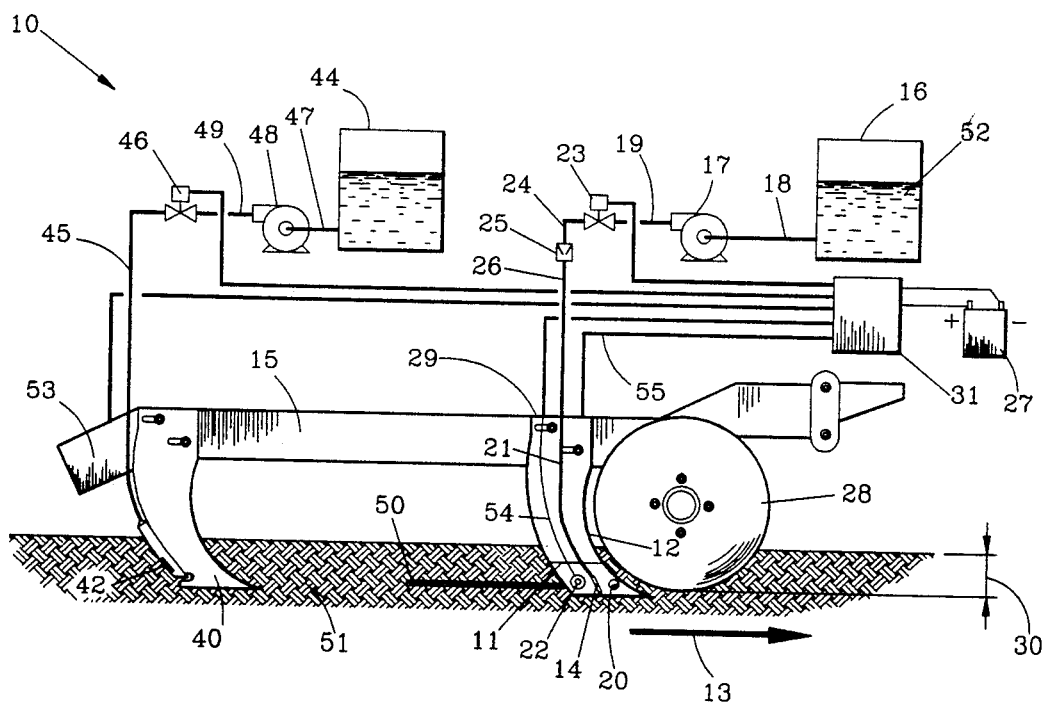
FIG. 2 is a functional representation of the sensing and application system with a schematic representation of a ground-engaging device.

Referring now to FIG. 2, the soil chemical sensor and control system 10 includes a ground-engaging soil sampler shank 12 which may take many different forms, such as a knife, harrow, cultivator tine or the like, and which normally penetrates the soil to a desired depth. The sampler shank 12 may have a thin and tapered longitudinal cross-section below region 11 to facilitate soil penetration and provide intimate soil, shank, solvent, and electrode contact. Said sampler shank may be configured for use in various types of farming operations such as conventional tillage, where rugged anhydrous ammonia application knives are used. In such an application, the soil sampler shank may consist of a commercially available anhydrous knife with the remaining elements of the ground engaging shank 12 of the preferred embodiment described herein made into a thin plate removably affixed to the sides of said anhydrous knife. In ridge-till farming, chemical application is done routinely with cultivators which have shoe-shaped ground engaging surfaces. The elements of the preferred embodiment can be suitably built into any of these existing tools. In no-till farming, application may be conducted in the presence of surface residual crop debris, requiring a leading coulter 28 to provide an unencumbered path. For this type of farming, laterally adjustable mounting means 29 is necessary to insure that at least one side of shank 12 is held against a side of the kerf 30 produced by the passage of coulter 28 through the soil 51.

In the preferred embodiment, the sampler shank 12 may be formed of a multivalent conductive material, such as iron, and may serve as the larger of the electrodes that applies a voltage differential or current across and through the solvent-produced leachate and into the engaged soil 51. The ground-engaging soil sampler shank 12 is connected to support member 15 which, when coupled to chemical application vehicle 1 (FIG. 1) in motion, conveys the draft force necessary to move the system 10 through the soil 51 in the direction of arrow 13.

The ground-engaging soil sampler shank 12 preferably includes a solvent orifice 14 on at least one side thereof, and preferably on both sides, through which a solvent is forced that saturates adjacent soil to be sampled. A protrusion 20 which may be wedge shaped, hemispherical, cylindrical or the like is formed on the leading face of the sampler shank 12, immediately preceeding solvent orifice 14, and such protrusion 20 acts to prevent soil from clogging the solvent orifice 14 and to create a saturated path 50 in the soil as the sampler shank moves in the direction of arrow 13. The solvent 52 may be selected to target and limit the species analyzed from the soil extraction and voltage application or current penetration. When applying nitrogenous fertilizer, soil nitrate level is the chemical constituent preferably targeted and, consequently, the solvent may be aqueous because nitrates are highly soluble in water. Normally, most solvents used are aqueous solutions with additives especially selected for analysis of specific chemicals and/or operating utility. Even for nitrate analysis, solvents are not limited to water alone and may also contain additives such as $CaCl_2$ which, for example, can depress the freezing point of the solvent. Such additives are necessary should the sampler shank 12 be thermally connected or combined with the applicator shank 40 for economy and for the use of anhydrous ammonia fertilizer which produces reduced temperatures of the applicator shank 40 when delivered to the soil 51 through chemical delivery orifice 42. In a preferred embodiment, natural rainwater, collected in a non-contaminating cistern, is a suitable aqueous base. Such water normally has a pH of approximately 5.5 and is suitably buffered for hydrogen ions collected in the leachate. The solvent is supplied from a solvent storage container 16 which may embody any suitable material that is non-reactive with the solvent. Solvent supply container 16 communicates with pressure pump 17 via conduit 18. Downstream of pump 17 the solvent, under pressure, flows through manifold 19 to the inlet of flow control valve 23 which is preferably a fast response solenoid or butterfly type throttling valve.

In response to electrical signals from control means 31, the desired amount of solvent for soil saturation at tractor speed is released through the valve 23 which supplies a manifold 24 and then to a fixed orifice 25 therefrom by conduit 26 connected to the ground engaging soil sampler shank 12 via affixed conduit 21 and therefrom out to solvent orifice 14 on both sides of the sampler shank. A desireable amount of solvent released is, in the case of nitrate analysis, approximately 300 ml/minute for each solvent orifice 14 when the shank 12 is moving in the direction 13 at 8 mph. This amount is adequate to insure that the chemical constituent being sensed goes into solution, that is to say, an excess of solvent should be used. Such excess will insure that the saturated path 50 is at all times conductive for current penetration of the soil 51, even as farm vehicle ground speed varies, and that the applied voltage differential or current withdraws soil chemicals of interest from the soil 51.

A multivalent electrode 22, which is not required to be inert to the chemical species of interest, is preferably composed of a metal material dissimilar to that of the shank, has its conducting surface(s) horizontally aligned with, and spaced rearward from, solvent orifice 14. While rigidly but removably attached to sampler shank 12, said multivalent material electrode 22 is nonetheless electrically insulated therefrom and connected to control means 31 via conduit-protected wiring 54. Multivalent material electrode 22 may be positioned rearward or behind solvent orifice 14 such that as sampler shank 12 advances in the direction of arrow 13, the soil slurry, containing leachate promoted by solvent orifice 14, will make intimate contact with the sides of sampler shank 12, an action enhanced by the aforesaid tapered cross section and adjustable mounting means 29, said slurry ultimately reaching multivalent electrode 22 along saturated path 50. A voltage or current level obtained from control means 31 connected to power source 27 is impressed across multivalent electrode 22, which is preferably of a copper bearing material, and the multivalent iron electrode which is the body of shank 12. The body of shank 12 is connected to the opposite polarity reference of the power source 27 by wiring 55. With a fixed applied voltage, preferably within the range of about 1.4 to 1.8 volts potential difference, between said electrodes, of which the multivalent electrode 22 is held positive with respect to the body of shank 12, an electrical current will be conducted through the nitrate leachate slurry and into the soil at all times said slurry is in contact with both electrodes. The voltage potential can be selected to preclude current contributions from chemical species other than the desired species. The sampler shank 12 and its affixed, insulated electrode 22 are continuously subjected to both soil and soil slurry leachate abrasion as the support member 15 draws the soil chemical sensor and agricultural chemical delivery system 10 through the soil 51.

The sensing system disclosed herein has, in the real and practical world, two significant advantages: it is very fast acting, essentially instantaneous; and it is economical to implement. This system provides means for current sampling during a very short time period (typically less than a few thousandths of a second) to determine the resistivity of the combination of the soil resistivity and leachate slurry resistivity due to extracted, dissolved electrolytes, one of which is the target material to be assayed such as nitrate. The resistivity magnitude of the combined soil and leachate, when measured by applied voltage differential and current sampling methods, produces in the present invention an accurate relative measure of nitrate concentration in soils sampled at an effective time in the crop growth cycle. With shank 12 with electrode 22 operated at a 3" depth, and with the geometry of the preferred embodiment, the indicated resistivity is 160 ohm-m at an average soil nitrate concentration of 100 ppm.

The system just described and the method of using it within the present invention are deemed novel in every sense. The effects of additional negatively charged ion species which may occur in the leachate are ameliorated by our choice of preferred multivalent electrode materials, i.e., by a compound or alloy containing dissimilar multivalent materials such as copper for the positively polarized electrode and iron, the principal constituent of steel, for the negative electrode of this first technique. In addition, this electrode 22 specification has a high degree of specificity for the target nitrate ion which can be further enhanced by alternate means described herein.

Those skilled in the art will at once recognize that repeatable resistivity measurements are usually impossible using these simple electrodes in the conventional laboratory manner in a quiescent fluid. Such an effect is primarily the result of electode contamination and if left unchecked will indeed preclude accurate leachate resistivity measurement. The present invention removes this difficulty by the elegant expedient of aligning the geometry of the aforementioned orifice 14 and electrode 22 such that as the shank moves through the soil, the soil continously scours away electrochemical reaction products. Thus slurry resistivity is predictably measured very near time zero, which can be defined as the instant current begins to flow through the slurry.

At electrode 22, a selected multivalent material, such as a material containing copper, reacts with dilute nitric acid (nitrate solution) to yield nitric oxide as the principal product. The cell reaction occuring at the interface between electrode 22 and the leachate contained in the saturated path 50 is given by the equation:

$$3Cu + 8HNO_3 \rightarrow 3Cu(NO_3)_2 + 2NO(g) + 4H_2O$$

All of the reaction products listed on the right hand side of the equation are swept away by motion and abrasion from the electrode interface with the leachate and do not interfere with subsequent measurements. It is not necessary that electrode 22 be comprised of copper or an alloy of copper, and it will be recognized by those skilled in the art that many other materials are possible.

The resistivity sensitivity of a resulting electrode 22 can be further enhanced by applying a potential differing from the aforementioned fixed 1.4 to 1.8 volt range. It is advantageous to employ this mechanism in combination with soil resistivity measurements to provide both selectivity and sensitivity to nitrate species.

Figure 3:
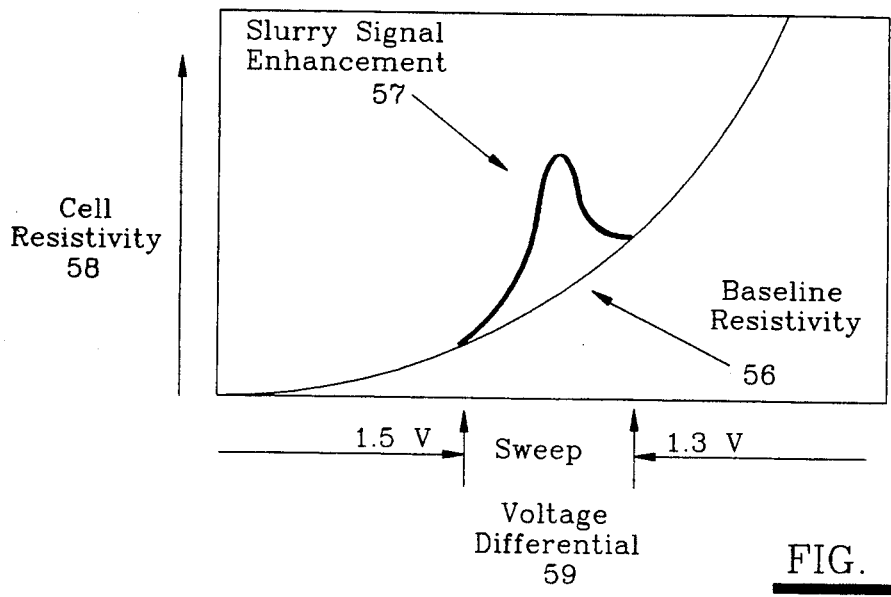
FIG. 3 portrays a typical electrochemical resistivity of a nitrate bearing soil as a function of voltage differential and the enhancement of such resistivity by the methods of the present invention.

Referring now to FIG. 3, the desired discrimination effect is illustrated by two different resistivity responses to a range of voltage differentials applied to moving electrodes in contact with the saturated path 50 of FIG. 2. Curve 56 illustrates the resistivity 58 of a nitrate bearing soil at a series of fixed voltage differentials. If the applied voltage, in the case of nitrate, is held fixed at some value within the 1.4 to 1.8 volt differential range 59, the indicated resistivity will follow the lower curve. If, however, the voltage range 59 is rapidly and alternately swept over the range between 1.3 and 1.5 volts, such as indicated by curve 57, there will be limited time for diffusion of nitrate to the electrodes. Apparent resistivity 58 will rise in response to the voltage differential change. This will be recognized by those skilled in the art as an expected electrochemical cell response. The choice of electrode material, preferably copper bearing alloys for electrode 22, will enhance this difference. In particular, it has been found that a copper electrode can double the indicated difference, compared to an iron multivalent electrode. Those skilled in the art will recognize that a DC voltage bias combined with a small AC component, typically 4000 Hz to accomodate the size and travel speed of electrode 22 in the preferred embodiment, is a suitable choice for this technique.

This technique is also useful should certain soil types be encountered in which an excess of water soluble species other than nitrate may exist. Under those conditions, the resistivity of the slurry may be drastically affected by one or more species in addition to nitrate when using only natural rainwater as a solvent. By adding an electrolyte, such as a buffered soluble phosphate solution, to the solvent, a different baseline resistivity response (dominated by the added soluble phosphate) similar to curve 56 will exist, and the variable voltage technique described above permits the resistivity of the nitrate contribution to be determined.

Returning now to FIG. 2, an applicator shank 40 having a shape generally similar to sampler shank 12 is attached to support member 15 such that applicator shank 40 cuts through the soil following the sampler shank to about the same depth and in approximate alignment therewith. At the soil penetrating end of applicator shank 40 is an orifice 42 through which fertilizer or other chemical additives may pass out into the soil. Said fertilizer or other chemical additive is stored in chamber 44 with the flow therefrom being controlled by flow control valve 46.

The control valve 46, preferably a fast acting type solenoid valve, may be rapidly opened and closed in response to a modulated output signal from sensing and control means 31. The sensing and control means 31 first determines the relative amount of the target chemical in the soil and the true ground speed of the farm vehicle by conventional speed detection means 53, preferably a non-contacting sensor, and then determines the amount of chemical additive to be applied to reach the level desired. The sensing and control means 31 then signals the chemical application control valve 46 to dispense the appropriate amount of fertilizer or other additive through conduit 42 driven by the pressure from chamber 44, in the case of anhydrous ammonia, or by additional pump means 48 installed between conduits 47 and 49 in the case of most agricultural chemicals and into the soil 51.

During equipment use the action is as follows. Support member 15 is hitched to the rear of a draft vehicle, typically a farm tractor, and both the ground engaging soil sampler shank 12 and the applicator shank 40 are lowered so that they penetrate the soil to a similar depth, preferably between zero and twelve inches. As the tractor moves in the direction of arrow 13, member 15 is drawn forward and attached shanks 12 and 40 proceed to slice through the soil. A tapered or wedge shape of sampler shank 12 will result in a saturated path 50 which maintains close contact with the sampler shank as it passes. Protrusion 20 prevents contacting soil from clogging solvent orifice 14 as solvent 52 is applied to the soil 51. The passing soil is saturated with solvent 52 exiting from solvent orifice 14 thereby creating a conductive saturated slurry path 50 as explained earlier. The forward motion of sampler shank 12 now causes the plume of conductive slurry to trail back in intimate contact with the iron body of shank 12 and ultimately to bridge the insulating gap between shank 12 (the iron electrode) and the positive potential electrode 22. A current proportional to the resistivity of the combination of the slurry and the soil itself will now flow between the electrodes which, as explained earlier, have impressed upon them a potential difference or current. Sensing and control means 31 measures said current passing through the leachate slurry and soil and therein derives therefrom a measure of resistivity, used in this example to assay nitrate concentration therein. The sensing and control means 31 instantly generates the required signal to drive control valve 46 and thus to dispense the appropriate amount of fertilizer or other chemical through orifice 42 as said orifice of applicator shank 40 passes adjacent the spot where the soil was tested but a moment previously.

In the preferred embodiment, soil chemical sensing and the corresponding application of fertilizer or other additives proceeds continously as the tractor traverses the field, thus providing a novel system for localized soil chemical testing and agricultural chemical application in real time. Indeed, the system 10 of the present invention provides a many-fold higher density of samplings per acre than can be cost-effectively provided via more conventional procedures. In fact, the soil chemical sensor and agricultural chemical delivery system 10 as reduced to practice before filing this application can provide up to three thousand chemical constituent assays per acre, using three of means 12, with the capability of directly integrated fertilizer and additive applications at each of the sample assay locations.

Figure 4:
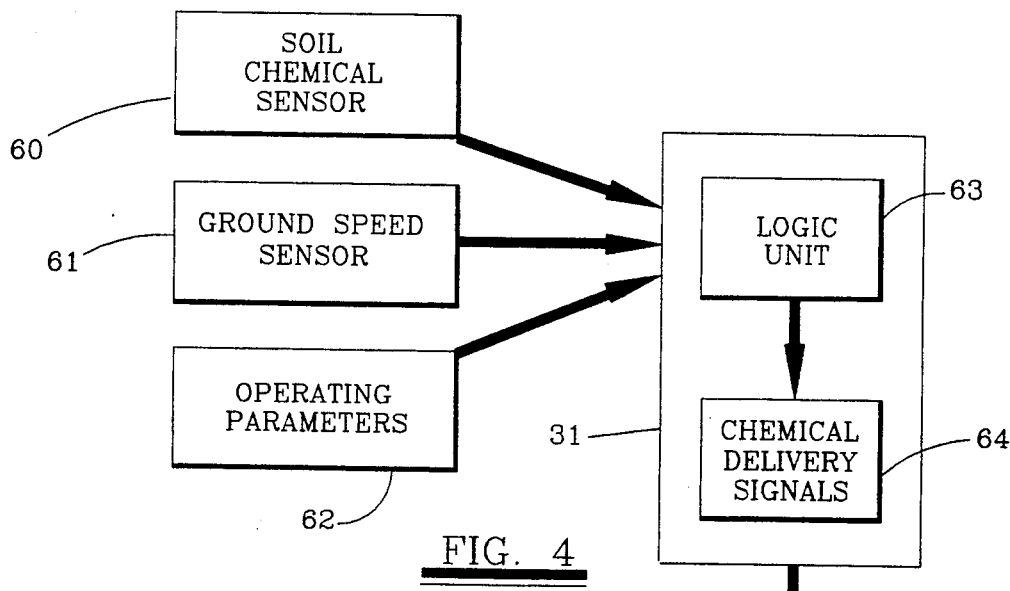
FIG. 4 is a schematic representation of the main sensory inputs, fixed inputs, and command outputs of the system.
Figure 5:
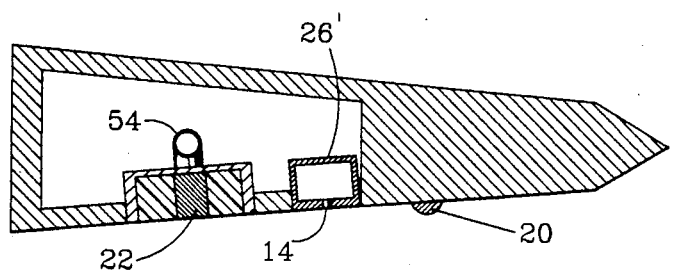
FIG. 5 is a cross-sectional representation of the soil sampler shank 12 of FIG. 2, taken at region 11.

Referring now to FIG. 4, which more generally describes the functions of control means 31, it may be seen that control means 31 is provided with two types of inputs. Preferably, rapidly varying field operation direct sensory data including soil chemical sensor data 60 from a plurality of sensors and true ground speed data from a single, generally non-contacting sensor 61 are measured electronically. Slowly varying or area sensitive operating parameters 62 are provided to control means 31 preferably by direct key entry by an operator or by means of electronic communication such as digital encoded data or direct analog voltages from external sources. Control means 31 interprets all sources of these data in its logic control unit 63, producing a series of chemical delivery signals 64 that are transmitted 65 to a plurality of chemical delivery valves and coordinated with the individual soil chemical sensor measurements made along the path of the sampler and applicator shanks.

Practical experience has shown that the first requirement of the sensing and control means is to respond to fluctuations in ground speed of the tractor. Agricultural chemical flow to each chemical applicator shank should be directly proportional to the ground speed of the tractor.

The maximum chemical flow rate from a complete tool assembly is determined by the equation:

$$Q_{max} = R_{max} * D * S,$$

where $Q_{max}$ equals the maximum chemical flow rate, D equals the lateral distance between adjacent chemical delivery shanks, and S equals true ground speed.

Input set point parameters 62 include, when fertilizing with nitrogen, the desired soil nitrate level as well as a maximum application rate, and the system 10 measures the nitrate in the ground during operation. Agronomic practice variables for both the desired soil nitrate level and maximum application rate are not expected to be constants over a farm field and may vary for example depending upon the planting time of the particular crop, the soil type or moisture holding capacity, or the hybrid variety grown in the field. These parameters are area-by-area farm production guidelines and do not fluctuate as widely as local soil chemical status; consequently, these input set points can either be manually set as constants or varied between production guidelines established for field subregions.

By comparing and subtracting the measured nitrate level from the desired maximum level, the sensing and control means 31 determines if nitrogen fertilizer needs to be added and adds it in proportion to the amount of nitrate already present. Because it is in no way desired to restrict the range of interpretation of the soil chemical data and the benefits to be derived therefrom, this interpretation can take the form most appropriate to maximizing benefits. For example, the classical exponential yield curve is but one form of theoretical crop response to soil chemical level. Quadratic and plateau models are also appropriate for benefit analysis. Alternate functional relationships in response to spatial nutrient variability may be employed to provide interpretation criteria for managing end use objectives such as minimizing ground water contamination and energy waste or maximizing field yield returns as well as crop quality.

In the preferred embodiment, a local fertilizer application rate (or sublocal) is set by first subtracting a local soil nitrate measurement $(NO_3^-)_{local}$ from the control setpoint $(NO_3^-)_{setpoint}$. Recommended application rates (for "zero" soil nitrate contribution or submaximum) are then adjusted by the ratio of this difference to the control setpoint. In mathematical form, the equation is:

$$R_{local} = \frac{[(NO_3^-)_{setpoint} - (NO_3^-)_{local}]}{(NO_3^-)_{setpoint}} * R_{maximum}$$

In the case of corn with a yield goal of 150 bushels per acre, a maximum nitrogen fertilizer application of 150 lbs per acre (at zero soil nitrate) and a maximum soil nitrate level of 120 ppm have been found to be representative operating parameters.

The actual flow rate of chemical applied by the applicator shank is then modified by the above equation, so that:

$$Q = R_{local} * D * S,$$

where Q equals the local chemical flow rate, D equals the lateral distance between adjacent shanks, and S equals the true ground speed.

The delay between the time the chemical leaves a control valve and the time it reaches the soil is a prime consideration for precision application. Referring again to FIG. 2, the length of conduit 45 between control valve 46 and orifice 42 is preferably kept as short as possible. Time delays result from the time necessary for the chemical to move to the orifice 42 in the shank 40 from the valve 46. If the nitrate level measured in the soil is high, the required flow rate will be low and the delay of application of chemical will be increased relative to soil conditions where the nitrate level is low. The selection of a minimum length for conduit 45, approximately 1 foot of ¼" tubing, ensures that maximum chemical delivery occurs at the points where the soil is the most deficient in soil chemical level and, accordingly, contributes the greatest incremental yield benefit and application precision.

In operation, it has proven beneficial to time "average" soil chemical sensor readings for interpretation by conventional agronomic practice and produce time-averaged flow conditions. Even this less site-specific averaging is superior to known systems that experience long activation time delays by not even responding to ground speed changes in less than 10–20 seconds.

Parallel readings may be averaged together also as a means of determining, at the same point in time, the soil nitrate used for the computation of chemical flow requirements. This process provides a truly representative sample for an area and is useful for comparison to conventionally derived soil chemical estimates for a soil region.

Referring again to FIG. 2, in practice it has been found that the preferred embodiment produces an averaged resistivity signal that is 10 to 30% lower than the anticipated correlation of nitrate with resistivity. This effect is due to the small contribution of soil particle resistivity to total slurry resistivity at saturation.

Calibration to eliminate this small error may be accomplished in several ways, one of which is to utilize the solvent flow capabilities of valve 23. Solvent flow, while the farm vehicle is moving, is suspended for a fraction of a second. The resulting resistivity determined is the contribution from the in situ soil particles. By instantaneously subtracting the reciprocal of the resistivity obtained with the slurry from the reciprocal of the resistivity obtained with no slurry in contact with the soil, an error correction can be made. Alternatively, the solvent flow may be uninterrupted and simply rapidly directed away from the path of the sensors and back again.

In practice, the preferred embodiment has proven beneficial without use of the described calibration feature. We have observed a correlation between soil nitrate level and indicated resistivity. Correlation rather than direct infield calibration has proven to be a satisfactory practical solution.

Alternatively, calibration for the same soil particle error can be effected by operating the system through a portion of a farm field and observing the indicated soil nutrient display on control means 31. The average observed reading may then be compared to a rapid colorimetric field test of soil samples obtained from the same portion of the field in which the soil chemical sensor and precision chemical application system was operated.

With this procedure, approximately 48¾" diameter soil cores to 12" depth are preferably taken and thoroughly mixed with a gallon of distilled water in a rubber bucket, the resulting slurry filtered and the extract tested using a minimum of three EM Quant® No. 10020-1 nitrate test strips, available from EM Science, Cherry Hill, N.J., which are then read in a Nitracheck ™ colorimetric strip reader, available from Medistron Ltd., Horsham, West Sussex, England. The resulting indicated nitrate reading from the display on control means 31 may then be scaled to agree with the averaged output of the three or more test strips.

By employing any of these or other calibration techniques, the previously described small error in the averaged resistivity signal may be reduced to an extremely small error; i.e., fertilizer or other agri-chemicals may be applied with extreme precision.

Other alternate forms of the present invention will suggest themselves from a consideration of the apparatus and practices hereinbefore disclosed. Accordingly, it should be clearly understood that the systems and techniques described in the foregoing explanations and depicted in the foregoing drawings are intended as exemplary embodiments of the invention and not as limitations thereto.

What is claimed is:

1. A method for sensing substantially instantaneously at least one chemical constituent of a soil while traversing a field of said soil and determining substantially simultaneously therewith an amount of corrective chemical to be added to said soil, comprising the steps of:

penetrating the soil of a first soil sample while traversing said sample;
applying a solvent to said first soil sample to create a leachate while traversing said sample;

applying a voltage differential across said leachate and determining a parameter proportional to said soil constituent while traversing said sample; and determining the amount of corrective chemical to be added to said sample while traversing said sample.

2. The method of claim 1 further comprising the steps of:

determining said parameter in the absence of said leachate;

comparing said parameter determined in the absence of said leachate with said parameter determined in the presence of said leachate; and calibrating the determination of said parameter determined in the presence of said leachate so as to compensate for said parameter in the absence of said leachate.

3. The method of claim 1 further comprising the step of:

adding the amount of corrective chemical to said soil sample while traversing said soil sample.

4. The method of claim 1 further comprising the step of:

applying a correlating factor to said parameter determined in the presence of said leachate in order to correlate said parameter to the approximate relative concentration of the soil constituent of interest.

5. The method of claim 4, further comprising the steps of:

receiving from an external source a signal corresponding to said correlating factor, and processing said signal into a form suitable for applying as said correlating factor.

6. The method of claim 4, further comprising the steps of:

receiving a signal generated from operator input information corresponding to said correlating factor, and processing said signal into a form suitable for applying as said correlating factor.

7. A system for sensing substantially instantaneously at least one chemical constituent of a soil while traversing a field of said soil and determining substantially simultaneously therewith an amount of corrective chemical to be added to said soil, comprising:

means for penetrating the soil while traversing a first soil sample;

means for supporting a plurality of multivalent electrodes at about the depth of said soil penetration means;

means for applying a solvent to a portion of the soil at about such depth and creating a leachate electrically coupling said electrodes to the soil sample surrounding said leachate; and means for applying a voltage differential across said leachate through said electrodes, whereby said system determines the magnitude of an electrochemical component of said leachate proportional to the chemical constituent thereof.

8. The system of claim 7 further comprising:

means for adding the amount of corrective chemical to said soil sample while traversing said soil sample.

9. A sensor system for sensing a chemical constituent of a soil, comprising:

shank means for penetrating the soil and supporting a multivalent electrode thereon, said shank means being at least partially formed of a multivalent conductive material;

means cooperating with said shank means for applying a solvent to a portion of the soil and creating a leachate electrically coupling said shank means and electrode to the soil surrounding said leachate; and means for applying a voltage differential across said leachate through said shank means and electrode and determining the magnitude of an electrochemical component of said soil proportional to the chemical constituent thereof.

10. The sensor data system of claim 9 wherein a soil penetrating end of said shank means is crescent shaped.

11. The sensor system of claim 9 wherein said cooperating means and said shank means comprise a shank having at least one aperture on a side thereof for providing fluid communication between said soil and a solvent supply connected to said aperture.

12. The sensor system of claim 11 further comprising soil shielding means adjacent said aperture for preventing soil from clogging said aperture.

13. The sensor system of claim 9 wherein said shank means and said electrodes are formed primarily of dissimilar multivalent conductive material.

14. The sensor system of claim 9 wherein said shank means and said electrodes are formed primarily of similar multivalent conductive material.

15. The sensor system of claim 9 wherein said shank means supports said multivalent electrode thereon in non-parallel alignment with the direction of forward motion of said shank means.

16. A system for sensing substantially instantaneously at least one chemical constituent of a soil while traversing a field of said soil and determining substantially simultaneously therewith an amount of corrective chemical to be added to said soil, comprising:

means for penetrating the soil while traversing a first soil sample;

means for applying a solvent to said first soil sample to create a leachate while traversing said soil sample;

means for applying a voltage differential across said leachate and determining a parameter proportional to said soil constituent while traversing said sample; and means for determining the amount of corrective chemical to be added to said sample while traversing said sample.

17. The system of claim 16 further comprising:

means for determining said parameter in the absence of said leachate;

means for comparing said parameter determined in the absence of said leachate with said parameter determined in the presence of said leachate; and means for calibrating the determination of said parameter determined in the presence of said leachate so as to compensate for said parameter in the absence of said leachate.

18. The system of claim 16 further comprising:

means for adding the amount of corrective chemical to said soil sample while traversing said soil sample.

19. The system of claim 16 further comprising:

means for applying a correlating factor to said parameter determined in the presence of said leachate in order to correlate said parameter to the approximate relative concentration of the soil constituent of interest.

20. The system of claim 19 further comprising:

means for receiving from an external source a signal corresponding to said correlating factor, and means for processing said signal into a form suitable for applying as said correlating factor.

21. The system of claim 19 further comprising:
means for receiving a signal generated from operator input information corresponding to said correlating factor, and
means for processing said signal into a form suitable for applying as said correlating factor.

22. A method for calibrating means for rapidly determining soil constituent concentrations while traversing a field of such soil, comprising the steps of:
penetrating the soil of a plurality of soil samples while respectively traversing such samples;
applying a solvent to said plurality of samples to create a plurality of leachates while traversing such samples;
appyling a potential across each said leachate and determining the respective values of a parameter proportional to said soil constituent while traversing such samples;
determining a first representative value of such respective values;
comparing said first representative value with a second representative value; and
calibrating the determination of said first representative value so as to compensate for said second representative value.

23. The method of claim 22, wherein said second representative value is determined from a plurality of soil samples obtained from the traversed portion of such field and analyzed by other means.

24. A system for calibrating means for rapidly determining soil constituent concentrations while traversing a field of such soil, comprising:
means for penetrating the soil of a plurality of soil samples while respectively traversing such samples;
means for applying a solvent to said plurality of samples to create a plurality of leachates while traversing such samples;
means for applying a potential across each said leachate and determining the respective values of a parameter proportional to said soil constituent while traversing such samples;
means for determining a first representative value of such respective values;
means for comparing said first representative value with a second representative value; and
means for calibrating the determination of said first representative value so as to compensate for said second representative value.

25. The system of claim 24, further comprising means for receiving a signal corresponding to input information representing said second representative value.

* * * * *